(12) United States Patent
Poma

(10) Patent No.: US 12,383,475 B2
(45) Date of Patent: Aug. 12, 2025

(54) MULTI-FRAGRANCE KIT

(71) Applicant: Bodyofwork, LLC, Miami, FL (US)

(72) Inventor: Gabriela Poma, Key Biscayne, FL (US)

(73) Assignee: Bodyofwork, LLC, Miami, FL (US)

( * ) Notice: Subject to any disclaimer, the term of this patent is extended or adjusted under 35 U.S.C. 154(b) by 0 days.

(21) Appl. No.: 18/988,280

(22) Filed: Dec. 19, 2024

(65) Prior Publication Data

US 2025/0205124 A1   Jun. 26, 2025

Related U.S. Application Data

(60) Provisional application No. 63/612,825, filed on Dec. 20, 2023.

(51) Int. Cl.
   *A61K 8/04* (2006.01)
   *A61Q 13/00* (2006.01)

(52) U.S. Cl.
   CPC .............. *A61K 8/046* (2013.01); *A61Q 13/00* (2013.01); *A61K 2800/884* (2013.01)

(58) Field of Classification Search
   CPC ... A61K 8/046; A61K 2800/884; A61Q 13/00
   USPC ......................................................... 512/4, 1
   See application file for complete search history.

(56) References Cited

U.S. PATENT DOCUMENTS

| 11,090,404 | B2 * | 8/2021 | Bush ....................... A61L 9/125 |
| 2013/0306752 | A1 | 11/2013 | Ruiz Ballesteros et al. |
| 2014/0352090 | A1 | 12/2014 | Schuchter et al. |
| 2017/0114298 | A1 | 4/2017 | Angel et al. |
| 2017/0151363 | A1 * | 6/2017 | Baxter .................... A61L 9/125 |

FOREIGN PATENT DOCUMENTS

WO   2023/165897 A1   9/2023

OTHER PUBLICATIONS

International Search Report and Written Opinion issued in related Application Serial No. PCT/US2024/061109 on Feb. 14, 2025.

* cited by examiner

*Primary Examiner* — Jessica Whiteley
(74) *Attorney, Agent, or Firm* — Brian J. Colandreo; Heath M. Sargeant; Holland & Knight LLP

(57) ABSTRACT

A multi-fragrance kit including: a first substance having a first fragrance; and a second substance having a second fragrance, wherein the second fragrance is a dialogue of the first fragrance.

17 Claims, 2 Drawing Sheets

MULTI-FRAGRANCE KIT

RELATED APPLICATION

This application claims the benefit of U.S. Provisional Application No. 63/612,825, filed on 20 Dec. 2023, the entire contents of which are herein incorporated by reference.

TECHNICAL FIELD

This disclosure relates to fragrances and, more particularly, to multi-fragrance kits.

BACKGROUND

Perfume, derived from the Latin "per fumum" (through smoke), has a rich history spanning thousands of years, beginning with ancient civilizations like the Egyptians, Mesopotamians, and Indus Valley cultures. Early perfumes were crafted from resins, woods, and aromatic plants, often used in religious rituals and burial ceremonies. The Egyptians pioneered perfumery as an art, blending oils with spices, flowers, and herbs to create fragrances for personal adornment and divine offerings. The craft later flourished in ancient Greece and Rome, where scents symbolized status and luxury. During the Islamic Golden Age, innovations in distillation refined perfumery, allowing for the extraction of essential oils, while the trade routes spread aromatic ingredients like ambergris, musk, and exotic spices to Europe. By the Renaissance, perfumery had become a symbol of sophistication in European courts, eventually evolving into a global industry in modern times.

Layering fragrances, though often seen as a contemporary trend, has historical roots as well. In the Middle East, where perfumery traditions are deeply entrenched, individuals have long combined oils, incense, and sprays to create unique, personal scents. This practice was influenced by the cultural significance of rich, multi-faceted aromas in religious and social contexts. Today, layering allows wearers to express individuality by blending complementary or contrasting scents, enhancing longevity, or transforming a fragrance's character. Whether through tradition or modern creativity, the history of perfume and layering illustrates humanity's enduring fascination with scent as a form of art and self-expression.

SUMMARY OF DISCLOSURE

In one implementation, a multi-fragrance kit includes: a first substance having a first fragrance; and a second substance having a second fragrance, wherein the second fragrance is a dialogue of the first fragrance.

One or more of the following features may be included. The second fragrance may be complementary of the first fragrance. The second fragrance may be contrasting of the first fragrance. The second fragrance may be interconnected with the first fragrance. A multi-chamber container may separately store the first substance and the second substance. The first substance may include one or more of: an aerosol; a cream; an oil; and a roll on. The second substance may include one or more of: an aerosol; a cream; an oil; and a roll on.

In another implementation, a multi-fragrance kit includes: a first substance having a first fragrance; and at least a second substance having at least a second fragrance, wherein the at least a second fragrance is a dialogue of the first fragrance.

One or more of the following features may be included. The at least a second fragrance may be complementary of the first fragrance. The at least a second fragrance may be contrasting of the first fragrance. The at least a second fragrance may be interconnected with the first fragrance. A multi-chamber container may separately store the first substance and the at least a second substance. The first substance may include one or more of: an aerosol; a cream; an oil; and a roll on. The at least a second substance may include one or more of: an aerosol; a cream; an oil; and a roll on.

In another implementation, a multi-fragrance kit includes: a first substance having a first fragrance; a second substance having a second fragrance, wherein the second fragrance is a dialogue of the first fragrance; and a multi-chamber container for separately storing the first substance and the second substance.

One or more of the following features may be included. The second fragrance may be complementary of the first fragrance. The second fragrance may be contrasting of the first fragrance. The second fragrance may be interconnected with the first fragrance. The first substance may include one or more of: an aerosol; a cream; an oil; and a roll on. The second substance may include one or more of: an aerosol; a cream; an oil; and a roll on The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Dialogue Scents

The concept of dialogue scents, where two or more fragrances are designed to interact with each other, has its roots in the evolving art of perfumery and the human desire to create layered, dynamic scent experiences. While the explicit idea of "dialogue" between fragrances is modern, its essence can be traced to historical practices. In ancient cultures, particularly in the Middle East and Asia, the layering of scented oils, incense, and attars created evolving aromatic profiles that mirrored this idea of interplay. These practices were rooted in both personal expression and cultural traditions, emphasizing harmony and contrast in scent.

In the 20th century, as modern perfumery advanced, the notion of complementary fragrances began to take form, often seen in the creation of scent duos for men and women. These pairs were designed to complement each other when worn individually or in proximity, reflecting a subtle interplay of masculine and feminine energies. In niche and luxury perfumery, this concept expanded further, with houses exploring the relationship between scents as layered narratives-using contrasting notes, shared themes, or sequential storytelling to evoke specific moods or memories.

Today, dialogue scents reflect a more nuanced approach to personalization and creativity. These dialogues celebrate the dynamic nature of scent, allowing it to evolve through interaction, much like a conversation between individuals. Whether through shared ingredients, contrasting profiles, or conceptual storytelling, the history of dialogue scents highlights the ever-innovative ways perfumers have sought to capture the complexity of human connection and self-expression.

Unfortunately, whether one scent is a dialogue of another scent is often not abundantly clear, requiring people to experiment with the combination of various scents to (hopefully) achieve the desired result. Accordingly, if multiple fragrances that are dialogues of each other are offered in a kit form, the uncertainty as to whether these fragrances will interact well with each other is eliminated.

Figure 1:
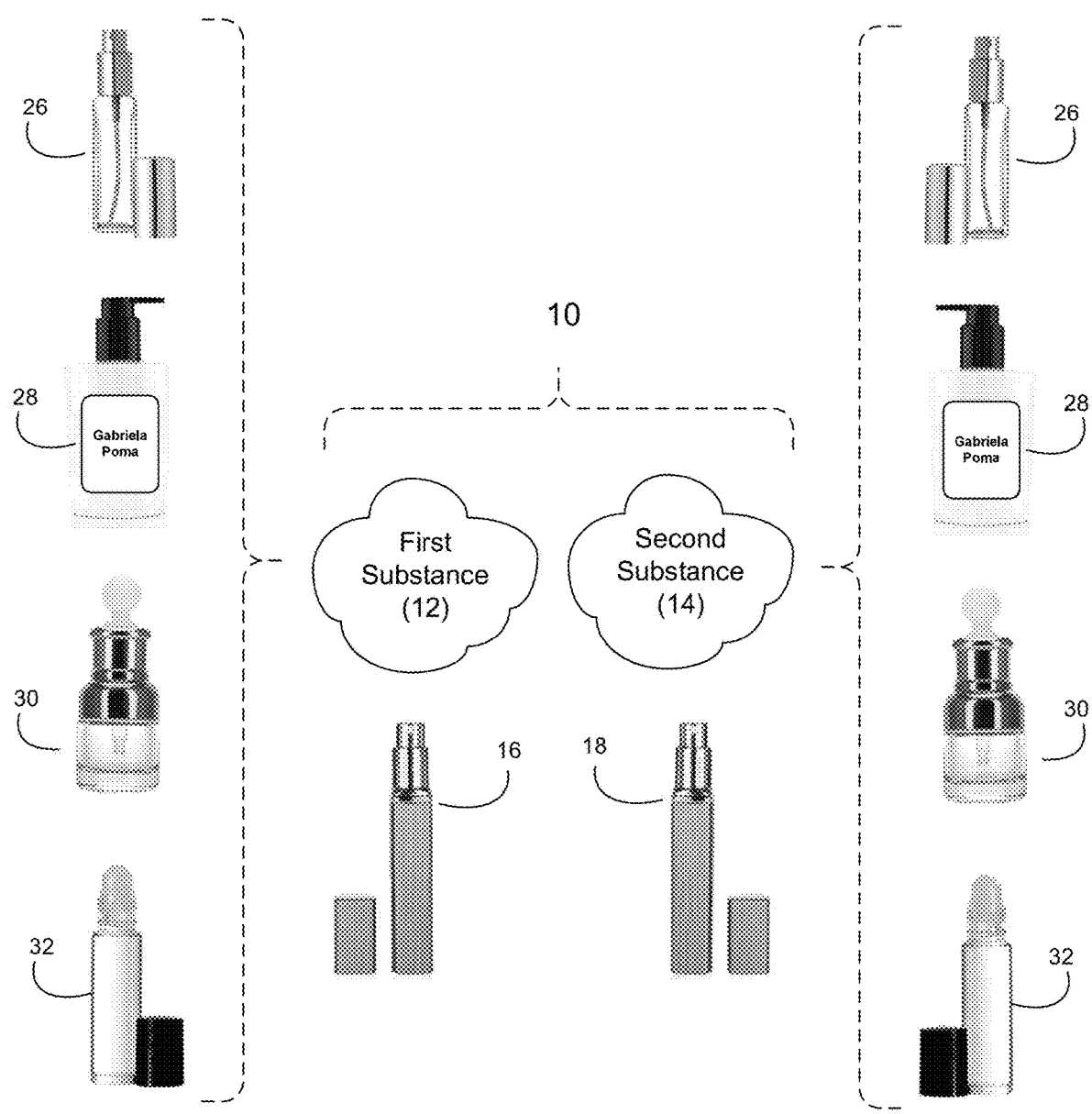
FIG. 1 is a diagrammatic view of a multi-fragrance kit according to an embodiment of the present disclosure.

Referring to FIG. 1, there is shown a multi-fragrance kit (e.g., multi-fragrance kit 10). The multi-fragrance kit (e.g., multi-fragrance kit 10) may include: a first substance (e.g., first substance 12) having a first fragrance and a second substance (e.g., second substance 14) having a second fragrance. The second fragrance of the second substance (e.g., second substance 14) may be a dialogue of the first fragrance of the first substance (e.g., first substance 12).

Two scents may be considered dialogues of each other if these two scents are complementary, contrasting, or interconnected in a way that creates a narrative or interplay between them. This concept of a dialogue is often used in perfumery to design scents that speak to one another, whether by evoking similar moods or by balancing each other's differences.

Characteristics of Scent Dialogues

1. Shared Notes or Accord Themes:
    Both scents may share one or more key notes (e.g., bergamot, jasmine, or sandalwood) but develop them differently. An example of such a scent dialogue may include a fresh citrus top note in one scent that evolves into a deep, woody base in the other scent.
2. Contrasting Profiles:
    One scent may be warm and rich, while the other scent may be cool and airy, creating a yin-yang effect. An example of such a scent dialogue may include a smoky, leather-based scent paired with a fresh aquatic scent.
3. Sequential Storytelling:
    The scents may represent different "chapters" in a story, like day vs. night, summer vs. winter, or youth vs. maturity. An example of such a scent dialogue may include a scent that embodies a morning's freshness paired with scent that embodies the cozy warmth of dusk.
4. Shared Purpose or Inspiration:
    Both fragrances may be inspired by the same theme (e.g., a location, emotion, or historical period) but interpreted differently. An example of such a scent dialogue may include a unisex pair inspired by a forest, where one focuses on mossy, green aspects, and the other on the smoky, resinous notes.
5. Layering Compatibility:
    The two scents may be designed to be layered, with each enhancing or transforming the other when combined. An example such a scent dialogue may include a soft floral fragrance paired with a spicy amber scent, creating a unique profile when worn together.
6. Gender-Neutral Pairings or Counterpoints:
    Fragrances that speak to traditional notions of masculinity and femininity but still complement one another. An example such a scent dialogue may include a crisp fougère and a sweet, powdery floral.

How to Create a Scent Dialogue

Use Contrasts Mindfully: Pair light and dark elements or bright and moody tones to create balance and intrigue.

Play with Progression: Make one scent feel like a continuation of the other.

Share DNA: Include a unifying ingredient or structure to tie them together while maintaining distinct personalities.

Various Examples of Scent Dialogues

Example 1: Sunrise and Sunset

Inspiration: The beginning and end of a warm, golden day.
Sunrise (Bright and Uplifting):
    Top Notes: Bergamot, Grapefruit, Orange Blossom
    Heart Notes: Neroli, Jasmine, Honey
    Base Notes: White Musk, Light Woods
    Profile: A zesty, citrusy scent with a soft floral dry-down to evoke the freshness and optimism of morning.
Sunset (Warm and Enveloping):
    Top Notes: Blood Orange, Cardamom
    Heart Notes: Tuberose, Amber
    Base Notes: Sandalwood, Vanilla, Tonka Bean
    Profile: A deeper, richer composition with warm spices and creamy woods to reflect the comforting glow of dusk.

Example 2: Ocean and Shore

Inspiration: The relationship between the sea and the land.
Ocean (Fresh and Aquatic):
    Top Notes: Sea Salt, Marine Accord, Lime
    Heart Notes: Seaweed, Lavender, Sage
    Base Notes: Driftwood, Ambergris
    Profile: Crisp, ozonic, and breezy, capturing the expansive nature of the sea.
Shore (Earthy and Grounded):
    Top Notes: Lemon Zest, Pink Pepper
    Heart Notes: Cypress, Vetiver, Green Tea.
    Base Notes: Oakmoss, Patchouli, Sand Accord
    Profile: Earthy and textured, evoking the rugged stability of the shoreline.

Example 3: Masculine and Feminine Yin-Yang

Inspiration: Contrasting yet harmonious energies in traditional masculine and feminine profiles.
Masculine (Woody and Smoky):
    Top Notes: Black Pepper, Grapefruit
    Heart Notes: Leather, Guaiac Wood
    Base Notes: Vetiver, Birch Tar, Cedarwood
    Profile: Bold, rugged, and smoky, leaning into traditional masculine codes.
Feminine (Soft and Sweet):
    Top Notes: Pear, Mandarin.
    Heart Notes: Rose, Ylang-Ylang, Almond Blossom
    Base Notes: Vanilla, Benzoin, Cashmere Musk
    Profile: Sweet, powdery, and enveloping, exuding warmth and softness.

Example 4: Seasons of the Year

Inspiration: A dialogue of changing seasons.
Spring (Green and Floral):
  Top Notes: Galbanum, Lemon, Mint.
  Heart Notes: Lily of the Valley, Magnolia, Peony
  Base Notes: Moss, Soft Amber
  Profile: Fresh and verdant, celebrating renewal and growth.
Autumn (Warm and Spicy):
  Top Notes: Clove, Cinnamon, Bergamot
  Heart Notes: Saffron, Dried Fruits
  Base Notes: Labdanum, Oud, Patchouli
  Profile: Rich and spicy, evoking falling leaves and cozy evenings.

Tips for Designing Scent Dialogues

Focus on Complementary Notes: Decide on a few unifying elements (e.g., citrus or amber) but explore different ways to highlight them in each scent.

Think in Layers: If the scents are intended to be layered, ensure their key components do not clash (e.g., avoid mixing two overly strong base notes).

Experiment with Narrative: What's the story or relationship between the two scents? Let the ingredients help tell it.

Use Opposites to Attract: Pair fresh with warm, bright with deep, or soft with bold for a dynamic interplay.

Accordingly, the second fragrance (of second substance 14) may be complementary of the first fragrance (of first substance 12). Further, the second fragrance (of second substance 14) may be contrasting of the first fragrance (of first substance 12). Additionally, the second fragrance (of second substance 14) may be interconnected with the first fragrance (of first substance 12).

Examples of the first substance (e.g., first substance 12) and/or the second substance (e.g., second substance 14) may include but are not limited to one or more of: an aerosol; a cream; an oil; and a roll on.

As is known in the art, fragrance products come in various formats, each designed to deliver scent in a unique way. An aerosol refers to a pressurized spray that disperses the fragrance as a fine mist, often used for body sprays or room fresheners. It provides a lightweight and evenly diffused scent, making it ideal for quick application. A cream, on the other hand, is a thicker, emollient-based product that combines fragrance with moisturizing ingredients. Applied directly to the skin, it offers a subtle and intimate scent while nourishing the skin, often used in layering routines to enhance longevity. A fragrance oil is a concentrated, alcohol-free form of perfume that delivers a rich and long-lasting scent. Typically applied to pulse points, it absorbs into the skin and evolves into a warmer, deeper aroma over time, making it ideal for a more personal and luxurious fragrance experience. Finally, a roll-on fragrance features a rollerball applicator, allowing for precise application of either alcohol-based perfumes or fragrance oils directly to the skin. Compact and portable, roll-ons are perfect for travel or on-the-go touch-ups, offering a subtle and personal scent throw.

The multi-fragrance kit (e.g., multi-fragrance kit 10) may include a plurality of containers for storing the first substance (e.g., first substance 12) and the second substance (e.g., second substance 14). For example, a first container (e.g., first container 16) may be configured to store the first substance (e.g., first substance 12), while a second container (e.g., second container 18) may be configured to store the second substance (e.g., second substance 14).

The manner in which the first container (e.g., first container 16) and/or the second container (e.g., second container 18) is configured may vary depending upon the type of substances (e.g., an aerosol; a cream; an oil; and a roll on).

Figure 2:
FIG. 2 is a diagrammatic view of a multi-chamber container of the multi-fragrance kit of FIG. 1 according to an embodiment of the present disclosure.

Referring also to FIG. 2, a multi-chamber container (e.g., multi-chamber container 20) may be configured to separately store the first substance (e.g., first substance 12) and the second substance (e.g., second substance 14). For example, the multi-chamber container (e.g., multi-chamber container 20) may include a first chamber (e.g., first chamber 22) for storing the first substance (e.g., first substance 12) and a second chamber (e.g., second chamber 24) for storing the second substance (e.g., second substance 14). This multi-chamber container (e.g., multi-chamber container 20) may be configured as a pair of nesting bottles (as shown in FIG. 2), wherein the top bottle functions as a cap for the bottom bottle. Alternatively, this multi-chamber container (e.g., multi-chamber container 20) may be configured as a pair of conjoined bottles (not shown), wherein the bottles are attached on one side.

The manner in which multi-chamber container (e.g., multi-chamber container 20) is configured my vary depending upon the type of substances (e.g., an aerosol; a cream; an oil; and a roll on).

For example, if the first substance (e.g., first substance 12) and/or the second substance (e.g., second substance 14) is an aerosol (e.g., aerosol 26), some or all of the first container (e.g., first container 16), the second container (e.g., second container 18) and/or the multi-chamber container (e.g., multi-chamber container 20) may be configured to dispense such an aerosol substance.

Further, if the first substance (e.g., first substance 12) and/or the second substance (e.g., second substance 14) is a cream (e.g., cream 28), some or all of the first container (e.g., first container 16), the second container (e.g., second container 18) and/or the multi-chamber container (e.g., multi-chamber container 20) may be configured to store such a cream substance.

Additionally, if the first substance (e.g., first substance 12) and/or the second substance (e.g., second substance 14) is an oil (e.g., oil 30), some or all of the first container (e.g., first container 16), the second container (e.g., second container 18) and/or the multi-chamber container (e.g., multi-chamber container 20) may be configured to dispense such an oil substance.

Further, if the first substance (e.g., first substance 12) and/or the second substance (e.g., second substance 14) is an roll-on (e.g., roll on 32), some or all of the first container (e.g., first container 16), the second container (e.g., second container 18) and/or the multi-chamber container (e.g., multi-chamber container 20) may be configured to dispense such a roll-on substance.

Further, it is foreseeable that the multi-chamber container (e.g., multi-chamber container 20) may be configured to simultaneously dispense the first substance (e.g., first substance 12) and the second substance (e.g., second substance 14). For example, if both the first substance (e.g., first substance 12) and the second substance (e.g., second substance 14) are aerosols, it is foreseeable that the multi-chamber container (e.g., multi-chamber container 20) may be configured to simultaneously dispense the first substance (e.g., first substance 12) and the second substance (e.g., second substance 14).

While the above-discussion concerns the multi-fragrance kit (e.g., multi-fragrance kit 10) including: a first substance (e.g., first substance 12) having a first fragrance and a second substance (e.g., second substance 14) having a second fragrance, this is for illustrative purposes only, as other configurations are possible and are considered to be within the scope of this disclosure. For example, the multi-fragrance kit (e.g., multi-fragrance kit 10) may include three or more substances having fragrances that are dialogues of each other. Additionally, it is foreseeable that the multi-fragrance kit (e.g., multi-fragrance kit 10) may include multiple groups of substances (e.g., a first group and a second group), wherein the substances in the first group have fragrances that are dialogues of the fragrances of the substances in the second group, thus allowing a user of multi-fragrance kit 10 to match various substances from each substance group to personalize their scent experience.

General:

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A multi-fragrance kit comprising:
   a first substance having a first fragrance;
   a second substance having a second fragrance, wherein the second fragrance is a dialogue of the first fragrance, wherein the second fragrance being the dialogue of the first fragrance includes the second fragrance forming a predefined scent pairing with the first fragrance; and
   a multi-chamber container for separately storing the first substance and the second substance, wherein a first chamber stores the first substance and the second chamber stores the second substance, wherein the first chamber and the second chamber form a pair of nesting chambers.

2. The multi-fragrance kit of claim 1 wherein the second fragrance is complementary of the first fragrance.

3. The multi-fragrance kit of claim 1 wherein the second fragrance is contrasting of the first fragrance.

4. The multi-fragrance kit of claim 1 wherein the second fragrance is interconnected with the first fragrance.

5. The multi-fragrance kit of claim 1 wherein the first substance includes one or more of:
   an aerosol;
   a cream;
   an oil; and
   a roll on.

6. The multi-fragrance kit of claim 1 wherein the second substance includes one or more of:
   an aerosol;
   a cream;
   an oil; and
   a roll on.

7. A multi-fragrance kit comprising:
   a first substance having a first fragrance, wherein the first substance is a cream; and
   at least a second substance having at least a second fragrance, wherein the at least a second fragrance is a dialogue of the first fragrance, wherein the at least a second fragrance being the dialogue of the first fragrance includes the at least a second fragrance forming a predefined scent grouping with the first fragrance; and
   a multi-chamber container for separately storing the first substance and the at least a second substance, wherein a first chamber stores the first substance and at least a second chamber stores the at least a second substance, wherein the multi-chamber container is configured to simultaneously dispense the first substance from the first chamber and the at least a second substance from the at least a second chamber.

8. The multi-fragrance kit of claim 7 wherein the at least a second fragrance is complementary of the first fragrance.

9. The multi-fragrance kit of claim 7 wherein the at least a second fragrance is contrasting of the first fragrance.

10. The multi-fragrance kit of claim 7 wherein the at least a second fragrance is interconnected with the first fragrance.

11. The multi-fragrance kit of claim 7 wherein the at least a second substance includes one or more of:
    an aerosol;
    a cream;
    an oil; and
    a roll on.

12. A multi-fragrance kit comprising:
    a first substance having a first fragrance;
    a second substance having a second fragrance, wherein the second fragrance is a dialogue of the first fragrance, wherein the second fragrance being the dialogue of the first fragrance includes the second fragrance forming a predefined scent pairing with the first fragrance; and
    a multi-chamber container for separately storing the first substance and the second substance, wherein a first chamber stores the first substance and the second chamber stores the second substance, wherein the first chamber and the second chamber form a pair of nesting chambers, wherein the first chamber forms a cap for the second chamber when nested together.

13. The multi-fragrance kit of claim 12 wherein the second fragrance is complementary of the first fragrance.

14. The multi-fragrance kit of claim 12 wherein the second fragrance is contrasting of the first fragrance.

15. The multi-fragrance kit of claim 12 wherein the second fragrance is interconnected with the first fragrance.

16. The multi-fragrance kit of claim 12 wherein the first substance includes one or more of:
    an aerosol;
    a cream;
    an oil; and
    a roll on.

17. The multi-fragrance kit of claim 12 wherein the second substance includes one or more of:
   an aerosol;
   a cream;
   an oil; and
   a roll on.

* * * * *